(12) United States Patent
Eto

(10) Patent No.: US 12,066,417 B2
(45) Date of Patent: Aug. 20, 2024

(54) LEARNING MODEL GENERATION SUPPORT APPARATUS, LEARNING MODEL GENERATION SUPPORT METHOD, AND COMPUTER-READABLE RECORDING MEDIUM

(71) Applicant: NEC CORPORATION, Tokyo (JP)

(72) Inventor: Riki Eto, Tokyo (JP)

(73) Assignee: NEC CORPORATION, Tokyo (JP)

( * ) Notice: Subject to any disclaimer, the term of this patent is extended or adjusted under 35 U.S.C. 154(b) by 837 days.

(21) Appl. No.: 17/251,337

(22) PCT Filed: Jun. 29, 2018

(86) PCT No.: PCT/JP2018/024931
§ 371 (c)(1),
(2) Date: Dec. 11, 2020

(87) PCT Pub. No.: WO2020/003532
PCT Pub. Date: Jan. 2, 2020

(65) Prior Publication Data
US 2021/0255156 A1    Aug. 19, 2021

(51) Int. Cl.
*G06N 20/00*    (2019.01)
*G01N 33/00*    (2006.01)
(Continued)

(52) U.S. Cl.
CPC ..... *G01N 33/0034* (2013.01); *G05B 13/0265* (2013.01); *G05B 13/048* (2013.01); *G06N 20/00* (2019.01)

(58) Field of Classification Search
None
See application file for complete search history.

(56) References Cited

U.S. PATENT DOCUMENTS

2008/0256008 A1*  10/2008  Kwok ............... G06N 3/004
                                                      706/20
2012/0143804 A1*   6/2012  Haddad ............ G06N 20/00
                                                      706/20

FOREIGN PATENT DOCUMENTS

CN    104914720 A    9/2015
JP    10-170422 A    6/1998
(Continued)

OTHER PUBLICATIONS

MSS alliance launched to set de facto standard for odor-sensing systems—aiming to establish basic elements of MSS technology towards practical use—[online], Sep. 29, 2015, NEC Corp., [viewed on Sep. 1, 2015], Internet <URL: http://jpn.nec.com/press/201509/20150929_01.html>.

(Continued)

*Primary Examiner* — Xuyang Xia
(74) *Attorney, Agent, or Firm* — Sughrue Mion, PLLC

(57) ABSTRACT

A learning model generation support apparatus 10 is an apparatus for supporting generation of a learning model to be utilized in odor detection using an odor sensor that reacts to a plurality of types of odors. The learning model generation support apparatus 10 includes a data acquisition unit 11 that acquires sensor data output by the odor sensor under specific measurement conditions and condition data specifying the measurement conditions, and inputs, as training data, the acquired sensor data and condition data to a machine learning engine 31 that generates the learning model, and a condition setting unit 12 that acquires a predictive accuracy output by the machine learning engine in response to input of the training data, and sets new measurement conditions for when the odor sensor newly outputs sensor data as training data, based on the acquired predictive accuracy.

15 Claims, 7 Drawing Sheets

(51) Int. Cl.
     *G05B 13/02*      (2006.01)
     *G05B 13/04*      (2006.01)

(56) References Cited

FOREIGN PATENT DOCUMENTS

| | | | |
|---|---|---|---|
| JP | 2001-305088 | A | 10/2001 |
| JP | 2005-337816 | A | 12/2005 |
| JP | 5582803 | B2 | 9/2014 |
| JP | 6121014 | B2 | 4/2017 |
| WO | 2009/157187 | A1 | 12/2009 |
| WO | WO-2017150917 | A1 * | 9/2017 .............. A61L 9/03 |
| WO | WO-2018138880 | A1 * | 8/2018 ............. G05B 13/04 |

OTHER PUBLICATIONS

International Search Report of PCT/JP2018/024931 dated Oct. 2, 2018 [PCT/ISA/210].
Written Opinion of PCT/JP2018/024931 dated Oct. 2, 2018 [PCT/ISA/237].
English translation of Written opinion for PCT Application No. PCT/JP2018/024931, mailed on Oct. 2, 2018.

* cited by examiner

LEARNING MODEL GENERATION SUPPORT APPARATUS, LEARNING MODEL GENERATION SUPPORT METHOD, AND COMPUTER-READABLE RECORDING MEDIUM

CROSS REFERENCE TO RELATED APPLICATIONS

This application is a National Stage of International Application No. PCT/JP2018/024931, filed Jun. 29, 2018.

TECHNICAL FIELD

The present invention relates to a learning model generation support apparatus and a learning model generation support method for supporting generation of a learning model for an odor sensor that detects odors from substances in the atmosphere, and further relates to a computer-readable recording medium having recorded thereon a program for realizing the apparatus and method.

BACKGROUND ART

Heretofore, odor sensors have been used in order to detect specific odors (e.g., refer to Patent Documents 1 and 2). An odor sensor detects a specific odor, by using a sensor element to detect an airborne chemical substance that produces the specific odor. Also, a metal oxide and an organic semiconductor thin film are given as examples of the sensor element. With such a sensor element, it becomes possible to detect a specific chemical substance, given that conductivity changes when the specific chemical substance adheres thereto.

Incidentally, with conventional odor sensors, there is a problem in that detectable chemical substances are fixed, and thus the odors that are detected are also fixed, resulting in a lack of versatility. In response, a Membrane-type Surface stress Sensor (MSS) that is able to detect a wide range of substances has been newly proposed in recent years (refer to Non-Patent Document 1).

An MSS is usually constituted by two or more MSS elements. Each MSS element includes a circular portion provided with a sensitive membrane, a frame surrounding the circular portion, and a plurality of bridges for coupling the circular portion to the frame. A piezoresistive element is embedded in each bridge. In such a configuration, the circular portion deforms due to stress occurring in the sensitive membrane when a substance sticks to the sensitive membrane, leading to stress being applied to the bridges. As a result, the electrical resistance of the piezoresistive elements embedded in the bridges changes greatly, thus enabling the substance stuck to the sensitive membrane to be detected from the resistance value.

Also, with an MSS, the material of the sensitive membrane differs for every MSS element, but this does not necessarily mean that the substance that sticks to each MSS element is fixed to one type. The material of the sensitive membrane of each MSS element is configured such that the pattern of output data of the entire MSS that is obtained by compositing the output data of the respective MSS elements differs according to the odor, that is, the set of substances constituting the odor. Thus, with an MSS, it becomes possible to detect many types of odors, by learning output patterns and generating learning models (analyzers), for every odor that is an analysis target, though machine learning in advance.

Also, with such odor sensors, application of edge computing, which has attracted attention in the Internet of Things (IoT) field in recent years, is effective in terms of the processing efficiency of sensor data. Specifically, this is because, in edge computing, sensor data can be collected with a small-scale computer system called an edge that is disposed comparatively close to the plurality of sensors. Also, this is because, in edge computing, the edge can made to perform preprocessing that includes data amount reduction processing and feature amount extraction processing, and a cloud can be made to perform analysis processing that uses analyzers.

LIST OF RELATED ART DOCUMENTS

Patent Document

Patent Document 1: Japanese Patent No. 6121014
Patent Document 2: Japanese Patent No. 5582803

Non-Patent Document

Non-Patent Document 1: MSS alliance launched to set de facto standard for odor-sensing systems—aiming to establish basic elements of MSS technology towards practical use—[online], Sep. 29, 2015, NEC Corp., [viewed on Sep. 1, 2015], Internet <URL: http://jpn.nec.com/press/201509/20150929_01.html>

SUMMARY OF INVENTION

Problems to be Solved by the Invention

Incidentally, odor sensors are characterized in that, even with the same analysis target, the behavior of the sensor data changes when measurement conditions such as temperature and humidity change. Thus, in order to enhance the detection accuracy of odor sensors, a learning model needs to be generated for every analysis target, by preparing as many variations as possible, as measurement conditions.

However, in reality it is difficult to prepare a large number of variations as measurement conditions. Furthermore, even if a large number of variations are prepared, there will be unnecessary measurement conditions as a consequence. Also, it is difficult to judge the number of variations needed to achieve sufficient detection accuracy.

An example object of the invention is to provide a learning model generation support apparatus, a learning model generation support method and a computer-readable recording medium that solve the above problems and can support setting of measurement conditions when generating a learning model for an odor sensor whose odor analysis target is not fixed.

Means for Solving the Problems

A learning model generation support apparatus according to an example aspect of the invention is an apparatus for supporting generation of a learning model to be utilized in odor detection using an odor sensor that reacts to a plurality of types of odors, the apparatus including:

a data acquisition unit configured to acquire sensor data output by the odor sensor under a specific measurement condition and the condition data specifying the measurement condition, and input the acquired sensor data and condition data, as training data, to a machine learning engine for generating the learning model; and a condition setting unit configured to acquire a predictive accuracy output by the machine learning engine in response to input of the training data, and based on the predictive accuracy, set a new measurement condition for when the odor sensor newly outputs sensor data as the training data.

Also, a learning model generation support method according to an example aspect of the invention is a method for supporting generation of a learning model to be utilized in odor detection using an odor sensor that reacts to a plurality of types of odors, the method including:

(a) a step of acquiring sensor data output by the odor sensor under a specific measurement condition and the condition data specifying the measurement condition, and inputting the acquired sensor data and condition data, as training data, to a machine learning engine for generating the learning model; and (b) a step of acquiring a predictive accuracy output by the machine learning engine in response to input of the training data, and based on the predictive accuracy, setting a new measurement condition for when the odor sensor newly outputs sensor data as the training data.

Furthermore, a computer-readable recording medium according to an example aspect of the invention is a computer-readable recording medium that includes a program recorded thereon for supporting generation of a learning model to be utilized in odor detection using an odor sensor that reacts to a plurality of types of odors, with a computer, the program including instructions that cause the computer to carry out:

(a) a step of acquiring sensor data output by the odor sensor under a specific measurement condition and the condition data specifying the measurement condition, and inputting the acquired sensor data and condition data, as training data, to a machine learning engine for generating the learning model; and (b) a step of acquiring a predictive accuracy output by the machine learning engine in response to input of the training data, and based on the predictive accuracy, setting a new measurement condition for when the odor sensor newly outputs sensor data as the training data.

Advantageous Effects of the Invention

As described above, according to the invention, setting of measurement conditions can be supported, when generating a learning model for an odor sensor whose odor analysis target is not fixed.

EXAMPLE EMBODIMENTS

Example Embodiment

Hereinafter, a learning model generation support apparatus, a learning model generation support method and a program in an example embodiment of the invention will be described, with reference to FIGS. 1 to 6.

Apparatus Configuration

Figure 1:
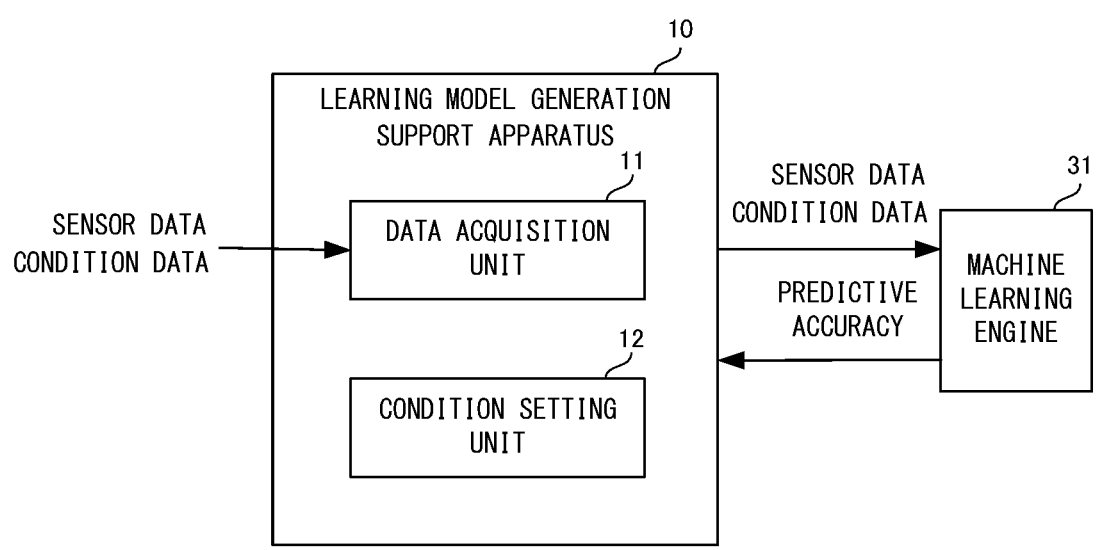
FIG. 1 is a block diagram showing a schematic configuration of a learning model generation support apparatus in an example embodiment of the invention.

Initially, a schematic configuration of the learning model generation support apparatus in the example embodiment will be described using FIG. 1. FIG. 1 is a block diagram showing a schematic configuration of the learning model generation support apparatus in the example embodiment of the invention.

A learning model generation support apparatus 10 in the example embodiment shown in FIG. 1 is an apparatus that supports generation of a learning model to be utilized in odor detection using an odor sensor. Also, the odor sensor that is used here is an odor sensor whose odor analysis target is not fixed, and outputs sensor data in reaction to a plurality of types of odors. Note that illustration of the odor sensor is omitted in FIG. 1.

As shown in FIG. 1, the learning model generation support apparatus 10 is provided with a data acquisition unit 11 and a condition setting unit 12. Of these, the data acquisition unit 11, first, acquires sensor data output by the odor sensor under specific measurement conditions, and condition data specifying those measurement conditions. Also, the data acquisition unit 11 inputs, as training data, the acquired sensor data and condition data to a machine learning engine 31 that generates a learning model.

The condition setting unit 12, first, acquires a predictive accuracy that is output by the machine learning engine 31 in response to input of training data. Also, the condition setting unit 12 sets new measurement conditions for when the odor sensor newly outputs sensor data as training data, based on the acquired predictive accuracy.

In this way, in the example embodiment, when machine learning using sensor data and measurement conditions corresponding thereto is performed by the machine learning engine, new measurement conditions are set, based on the learning result. In other words, according to the example embodiment, setting of measurement conditions can be supported, when generating a learning model for an odor sensor whose odor analysis target is not fixed, and, as a result, a highly accurate learning model will be built.

Figure 2:
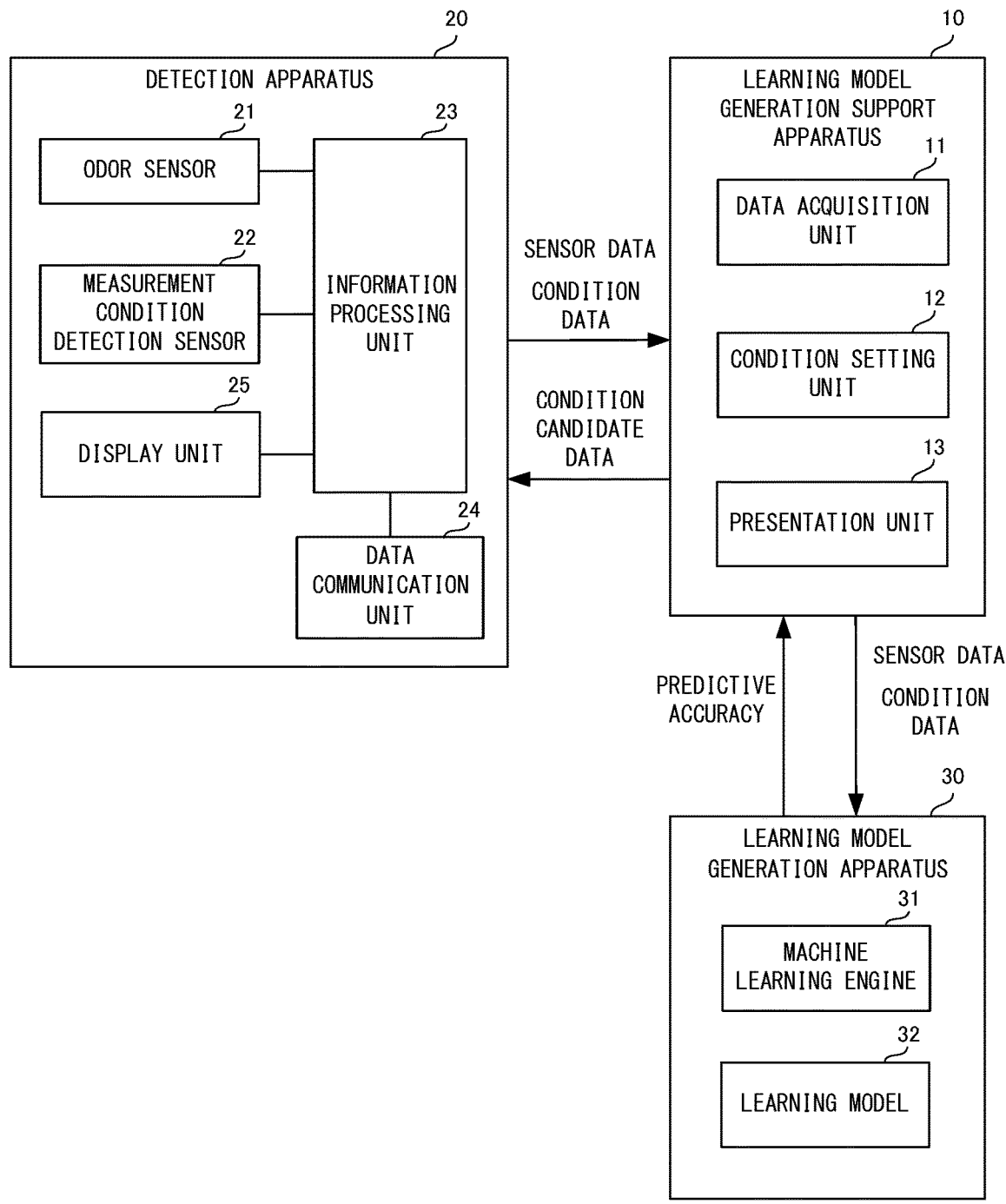
FIG. 2 is a block diagram showing a schematic configuration of the learning model generation support apparatus in the example embodiment of the invention.
Figure 3:
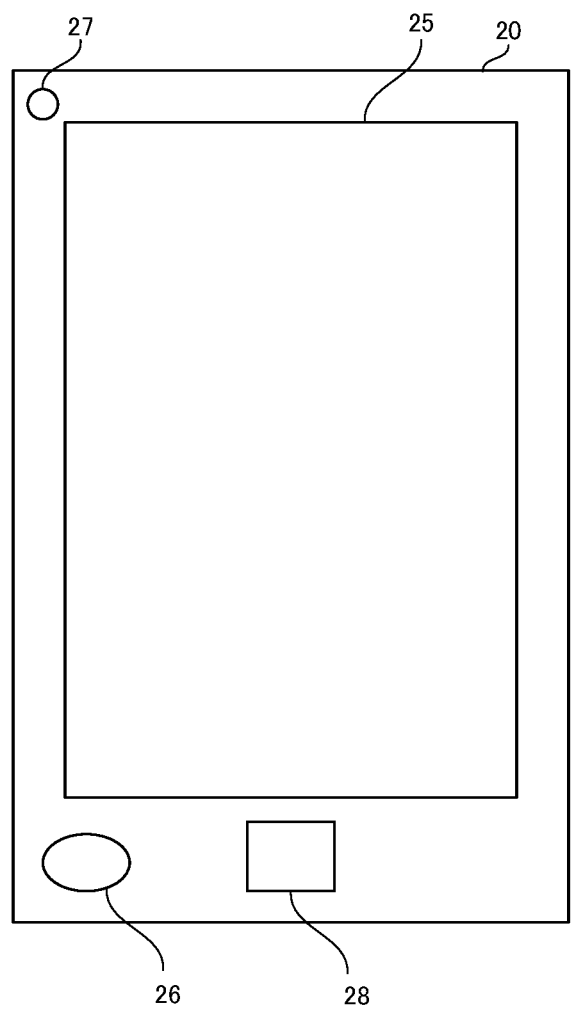
FIG. 3 is a diagram showing an example of a detection apparatus that is used in the example embodiment of the invention.

Next, the configuration and functions of the learning model generation support apparatus in the example embodiment will be more specifically described, using FIGS. 2 and 3. FIG. 2 is a block diagram showing a schematic configuration of the learning model generation support apparatus in the example embodiment of the invention.

As shown in FIG. 2, in the example embodiment, the learning model generation support apparatus 10 is connected to a detection apparatus 20 having an odor sensor 21 and a learning model generation apparatus 30 having the machine learning engine 31 in a manner that enables data communication.

The detection apparatus 20 is provided with the odor sensor 21, a measurement condition detection sensor 22, an information processing unit 23, a data communication unit 24, and a display unit 25. The detection apparatus 20, as a result of such a configuration, transmits sensor data output by the odor sensor 21 and condition data output by the measurement condition detection sensor 22 to the learning model generation support apparatus 10.

The abovementioned MSS is given as an example of the odor sensor 21. In the example embodiment, the odor sensor 21 is, however, not limited to an MSS, and may be any sensor that outputs sensor data in reaction to a plurality of types of odors.

The measurement condition detection sensor 22 detects the measurement conditions of the odor sensor 21, and outputs condition data specifying the detected measurement conditions as sensor data. The temperature and humidity ambient to the odor sensor 21 are given as examples of measurement conditions. In this case, a temperature sensor and a humidity sensor are used as the measurement condition detection sensor 22. Note that the measurement condition may be only temperature or only humidity. In these cases, only a temperature sensor or a humidity sensor is used.

Also, information on atmospheric gases ambient to the odor sensor, such as information relating to odors other than the odors to be detected, is also given as an example of a measurement condition. Atmospheric gases affect the accuracy of the odor sensor 21. Specifically, the component ratio of atmospheric gases, the concentration of each component, and the like are also given as examples, besides information relating to odors other than the odors to be detected. Furthermore, the distance from the odor sensor 21 to the target, the illuminance ambient to the odor sensor 21, the amount of ultraviolet light on the target, and the sampling period when measuring gases are also given as examples of measurement conditions.

The information processing unit 23, upon sensor data being output from the odor sensor 21 and condition data being output from the measurement condition detection sensor 22, performs digitization processing such as conversion to digital signals on this data. Also, the information processing unit 23 causes the data communication unit 24 to transmit the sensor data and condition data that have undergone digitization processing to the learning model generation support apparatus 10.

The data communication unit 24 is constituted by a communication device. Also, the display unit 25 is constituted by a display device such as a liquid crystal display.

FIG. 3 is a diagram showing an example of the detection apparatus that is used in the example embodiment of the invention. In the example in FIG. 3, a window 26 for guiding gases to be measured to the odor sensor 21 and a window 27 for the measurement condition detection sensor 22 are provided in the casing of the detection apparatus 20. Also, in FIG. 3, reference numeral 28 denotes an operation button of the detection apparatus 20.

The learning model generation apparatus 30 acquires sensor data output at the time of measurement and condition data specifying the measurement conditions, and inputs the acquired data to the machine learning engine 31 as training data. Note that the learning model generation apparatus 30 may acquire this data from the learning model generation support apparatus 10, or may acquire this data directly from the detection apparatus 20.

The machine learning engine 31, upon receiving input of training data, performs machine learning of the relationship between features of the sensor data and the measurement conditions by deep learning, a support vector machine, for example, and updates the parameters of a learning model 32.

Also, the machine learning engine 31 outputs the predictive accuracy together with updating the parameters. An F-score, Accuracy, Precision, Recall, the Receiver Operating Characteristic (ROC) curve, and the Area Under the Curve (AUC) are given as examples of predictive accuracy.

Of these, the F-score is an evaluation index of predictive accuracy, and is the harmonic mean of Precision and Recall. Accuracy indicates the rate at which correct answers were output in the prediction results as a whole. Precision indicates the rate of correct answers in the case where "true" was output. Recall indicates the rate at which "true" was the correct answer in the predictions as a whole. The ROC curve is a curve whose horizontal axis is the rate of false positives and whose vertical axis is as the rate of true positives. The AUC is the area of a region enclosed by the ROC curve, the horizontal axis, and the vertical axis.

When the learning model 32 has been built by the machine learning engine 31, the detection apparatus 20 is able to perform odor detection using this learning model 32. The detection result is displayed on a screen of the display unit 25.

Also, as shown in FIG. 2, the learning model generation support apparatus 10 is provided with a presentation unit 13, in addition to the abovementioned data acquisition unit 11 and condition setting unit 12. The presentation unit 13 presents new measurement conditions set by the condition setting unit 12.

Specifically, the presentation unit 13, upon new measurement conditions being set, transmits data (hereinafter, "condition candidate data") specifying the new measurement conditions to the detection apparatus 20. In this case, in the detection apparatus 20, the data communication unit 24 receives the condition candidate data, and passes this condition candidate data to the information processing unit 23. The information processing unit 23, upon receiving the condition candidate data, displays the new measurement conditions that are specified by the condition candidate data on the screen of the display unit 25.

In the example embodiment, the condition setting unit 12 sets new measurement conditions by executing Sequential Model-Based Optimization (SMBO) with predictive accuracy and measurement conditions as parameters, such that the predictive accuracy will be higher than the acquired predictive accuracy.

Specifically, the condition setting unit 12 sets new measurement conditions by executing a grid search or Bayesian optimization.

In the case of executing a grid search, the condition setting unit 12, first, sets a search space of the parameters divided into a grid, with the number of parameters (temperature, humidity and other measurement conditions) to be searched for as the dimension. The condition setting unit 12 then allocates a combination of the parameters for every grid point, executes simulation for every combination, and specifies the combination whose predictive accuracy is higher than the acquired predictive accuracy. The specified combination will be the new measurement conditions.

Also, in the case of executing Bayesian optimization, the condition setting unit 12, first, selects a combination of parameters to serve as a candidate, and executes simulation based on the selected combination of parameters. The condition setting unit 12 then selects another combination of parameters, based on this execution result, and executes simulation again. In other words, in this case, the condition setting unit 12 executes simulation while estimating parameters having a high possibility of being suitable, and specifies a combination to be the new measurement conditions.

Figure 4:
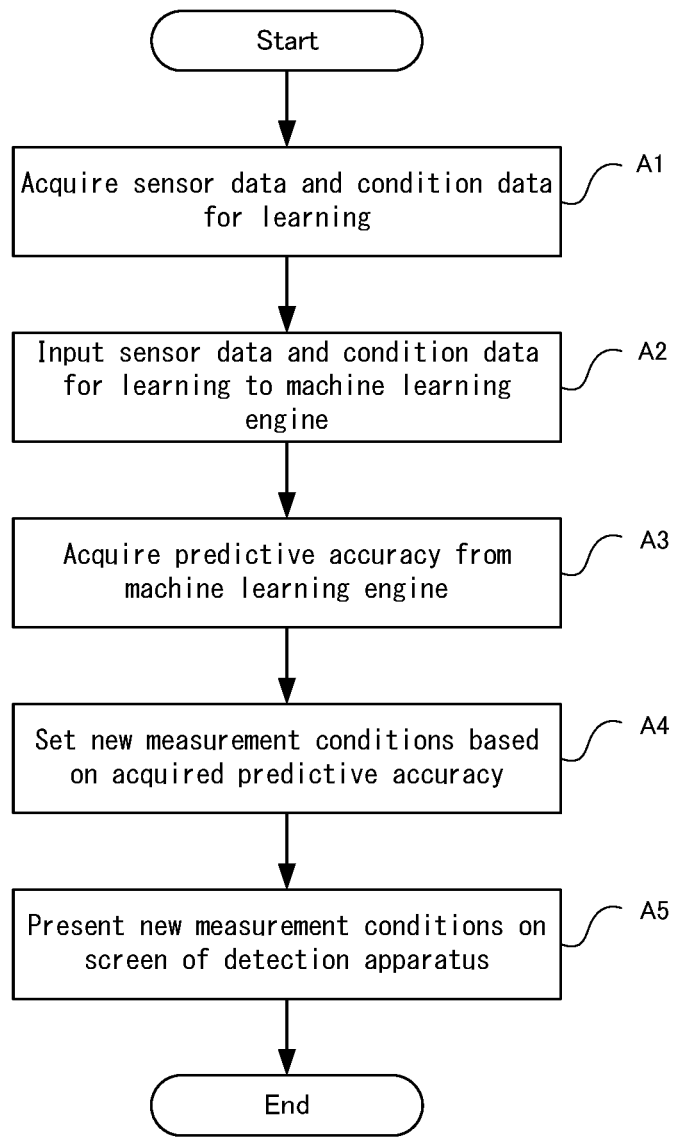
FIG. 4 is a flow diagram showing operations of the learning model generation support apparatus in the example embodiment of the invention.

Next, operations of the learning model generation support apparatus 10 in the example embodiment will be described using FIG. 4. FIG. 4 is a flow diagram showing operations of the learning model generation support apparatus in the example embodiment of the invention. In the following description, FIGS. 1 to 3 will be referred to as appropriate. Also, in the example embodiment, a learning model generation support method is implemented by operating the learning model generation support apparatus 10. Therefore, description of the learning model generation support method in the example embodiment will be replaced by the following description of the operations of the learning model generation support apparatus 10.

As shown in FIG. 4, initially, the data acquisition unit 11 acquires, as training data, sensor data output by the odor sensor 21 under specific measurement conditions and condition data specifying those measurement conditions (step A1).

Next, the data acquisition unit 11 inputs the sensor data and condition data acquired in step A1 to the machine learning engine 31 of the learning model generation apparatus 30 as training data (step A2). When step A2 has been executed, the machine learning engine 31 executes machine learning using the input training data.

Next, the condition setting unit 12, after execution of step A2, acquires the predictive accuracy that is output by the machine learning engine 31 in response to input of the training data, from the learning model generation apparatus 30 (step A3).

Next, the condition setting unit 12 sets new measurement conditions for when the odor sensor newly outputs sensor data as training data, based on the predictive accuracy acquired in step A3 (step A4).

Specifically, in step A4, the condition setting unit 12 executes sequential model-based optimization with predictive accuracy and measurement conditions as parameters, such that the predictive accuracy will be higher than the acquired predictive accuracy.

Next, the presentation unit 13 presents the new measurement conditions set in step A4 on the screen of the detection apparatus 20 (step A5).

Specifically, in step A5, the presentation unit 13, upon new measurement conditions being set, transmits condition candidate data specifying the new measurement conditions to the detection apparatus 20. In the detection apparatus 20, the data communication unit 24 thereby receives the condition candidate data, and passes this condition candidate data to the information processing unit 23. The information processing unit 23, upon receiving the condition candidate data, displays the new measurement conditions specified by this condition candidate data on the screen of the display unit 25.

Figure 5A:
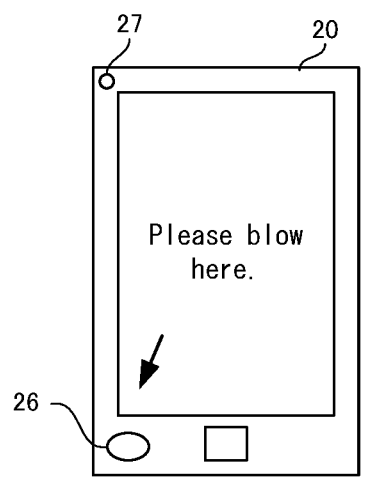
FIGS. 5A to 5C show examples of information that is displayed on a screen of the detection apparatus in the example embodiment of the invention.
Figure 5B:
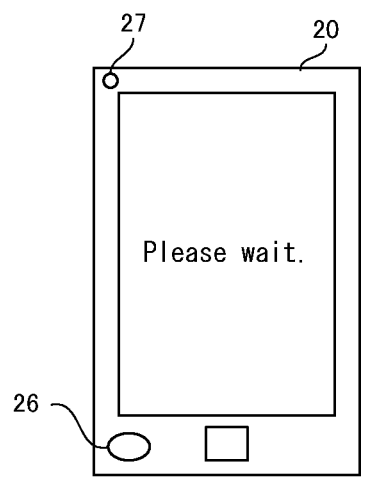
Figure 5C:
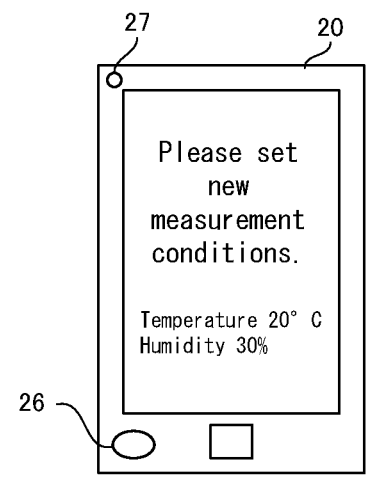

FIGS. 5A to 5C show examples of information that is displayed on the screen of the detection apparatus in the example embodiment of the invention. For example, when steps A1 to A5 have been executed, information supporting operations by the user for generating training data and new measurement conditions are displayed on the screen of the detection apparatus 20, as shown in FIGS. 5A to 5C. Also, the examples in FIGS. 5A to 5C show the case where the user's breath is the detection target.

Effects of Example Embodiment

As described above, according to the example embodiment, whenever machine learning is performed by the machine learning engine 31, more optimal measurement conditions are set, and the set measurement conditions are presented to the user of the detection apparatus 20. In other words, when a user generates a learning model for the odor sensor 21, the user is able to receive support in setting measurement conditions. As a result, a highly accurate learning model is readily built.

[Variation]

Figure 6:
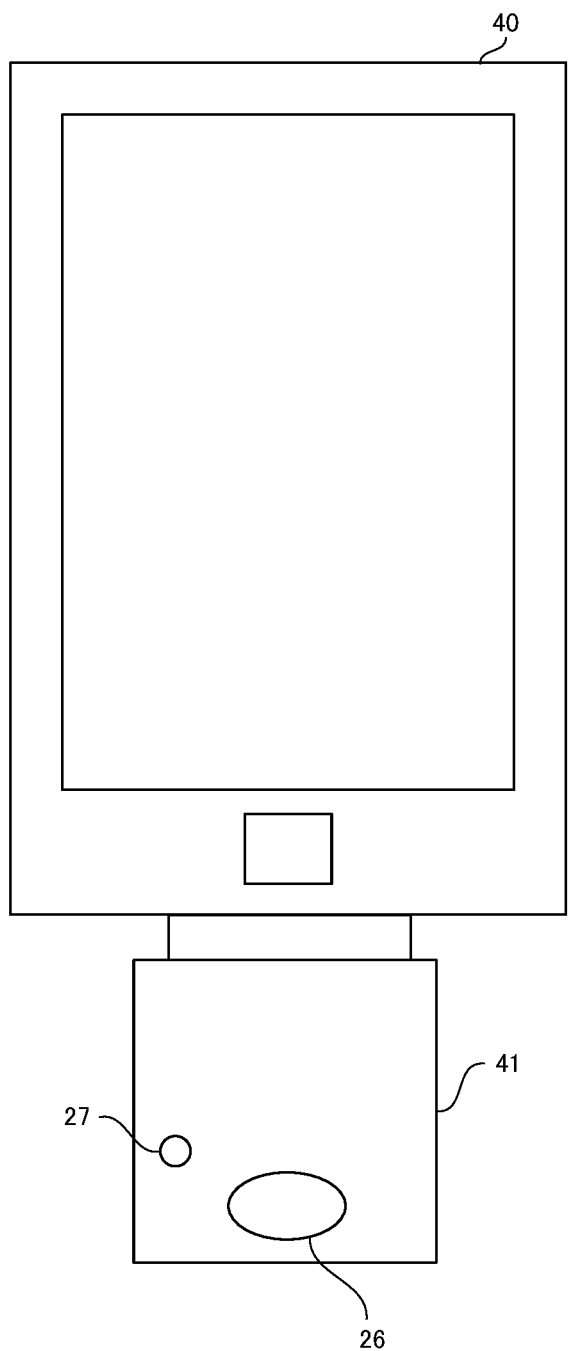
FIG. 6 is a diagram showing another example of the detection apparatus that is used in the example embodiment of the invention.

Here, another example of the detection apparatus 20 that is used in the example embodiment will be described using FIG. 6. FIG. 6 is a diagram showing another example of the detection apparatus that is used in the example embodiment of the invention.

In the example in FIG. 6, the detection apparatus 20 is provided with a communication terminal 40 such as a smartphone and a sensor unit 41. The odor sensor and the measurement condition detection sensor are housed in the casing of the sensor unit 41. Also, the sensor unit 41 is connected to the communication terminal 40 via an interface for externally connecting the communication terminal 40. In the example in FIG. 6, a processor provided in the communication terminal 40 functions as the information processing unit 23.

According to this variation, detection of substances in the atmosphere can be executed, by connecting the sensor unit 41 to a general-purpose communication terminal 40. Also, the sensor unit 41 is directly connected to the communication terminal 40 in this variation, but the connection therebetween need only be implemented in a manner that enables communication, and may be implemented wirelessly or by cable.

[Program]

A program according to the example embodiment need only be a program that causes a computer to execute steps A1 to A5 shown in FIG. 4. The learning model generation support apparatus 10 and the learning model generation support method in the example embodiment can be realized by this program being installed on a computer and executed. In this case, a processor of the computer performs processing while functioning as the data acquisition unit 11, the condition setting unit 12, and the presentation unit 13.

Also, the program in the example embodiment may be executed by a computer system built from a plurality of computers. In this case, for example, the computers may respectively function as one of the data acquisition unit 11, the condition setting unit 12, and the presentation unit 13.

Figure 7:
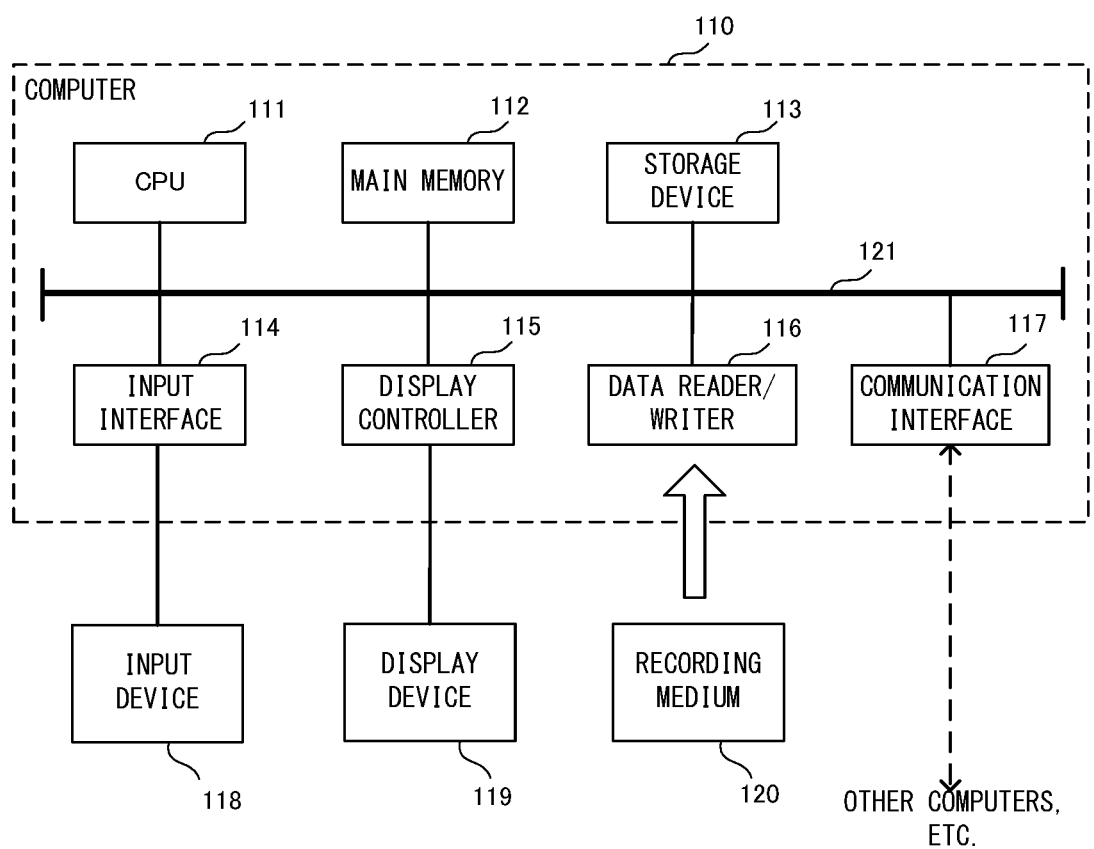
FIG. 7 is a block diagram showing an example of a computer that realizes the learning model generation support apparatus in the example embodiment of the invention.

Here, a computer that realizes the learning model generation support apparatus by executing the program in the example embodiment will be described using FIG. 7. FIG. 7 is a block diagram showing an example of a computer that realizes the learning model generation support apparatus in the example embodiment of the invention.

As shown in FIG. 7, a computer 110 includes a CPU (Central Processing Unit) 111, a main memory 112, a storage device 113, an input interface 114, a display controller 115, a data reader/writer 116, and a communication interface 117. These units are connected in a manner that enables data communication, via a bus 121. Note that the computer 110 may include a GPU (Graphics Processing Unit) or an FPGA (Field-Programmable Gate Array), in addition to the CPU 111 or instead of the CPU 111.

The CPU 111 implements various computational operations, by extracting a program (codes) according to the example embodiment stored in the storage device 113 to the main memory 112, and executing these codes in predetermined order. The main memory 112, typically, is a volatile storage device such as a DRAM (Dynamic Random Access Memory). Also, programs in the example embodiment are provided in a state of being stored on a computer-readable recording medium 120. Note that programs in the example embodiment may be distributed over the Internet connected via the communication interface 117.

Also, a semiconductor storage device such as a flash memory is given as a specific example of the storage device 113, other than a hard disk drive. The input interface 114 mediates data transmission between the CPU 111 and input devices 118 such as a keyboard and a mouse. The display controller 115 is connected to a display device 119 and controls display by the display device 119.

The data reader/writer 116 mediates data transmission between the CPU 111 and the recording medium 120, and executes readout of programs from the recording medium 120 and writing of processing results of the computer 110 to the recording medium 120. The communication interface 117 mediates data transmission between the CPU 111 and other computers.

Also, general-purpose semiconductor storage devices such as a CF (Compact Flash (registered trademark)) card and an SD (Secure Digital) card, magnetic recording media such as a flexible disk, and optical recording media such as a CD-ROM (Compact Disk Read Only Memory) are given as specific examples of the recording medium 120.

Note that the learning model generation apparatus 10 in the example embodiment is also realizable by using hardware corresponding to the respective units, rather than by a computer on which programs are installed. Furthermore, the learning model generation apparatus 10 may be realized in part by programs, and the remaining portion may be realized by hardware.

The example embodiment described above can be partially or wholly realized by supplementary notes 1 to 18 described below, although the invention is not limited to the following description.

(Supplementary Note 1)

A Learning Model Generation Support Apparatus for Supporting Generation of a Learning Model to be Utilized in Odor Detection Using an Odor Sensor that Reacts to a Plurality of Types of Odors, the Apparatus Including:

a data acquisition unit configured to acquire sensor data output by the odor sensor under a specific measurement condition and condition data specifying the measurement condition, and input the acquired sensor data and the condition data, as training data, to a machine learning engine for generating the learning model; and a condition setting unit configured to acquire a predictive accuracy output by the machine learning engine in response to input of the training data, and based on the predictive accuracy, set a new measurement condition for when the odor sensor newly outputs sensor data as the training data.

(Supplementary Note 2)

The learning model generation support apparatus according to supplementary note 1, in which the condition setting unit sets the new measurement condition, such that a predictive accuracy will be higher than the acquired predictive accuracy.

(Supplementary Note 3)

The learning model generation support apparatus according to supplementary note 2, in which the condition setting unit sets the new measurement condition, by executing sequential model-based optimization with the predictive accuracy and the measurement condition as parameters.

(Supplementary Note 4)

The learning model generation support apparatus according to any of supplementary notes 1 to 3, in which the measurement condition includes at least temperature and humidity ambient to the odor sensor.

(Supplementary Note 5)

The learning model generation support apparatus according to supplementary note 4, in which the measurement condition further includes information relating to an odor ambient to the odor sensor, other than an odor to be detected.

(Supplementary Note 6)

The learning model generation support apparatus according to any of supplementary notes 1 to 5, further including a presentation unit configured to present the set measurement condition.

(Supplementary Note 7)

A learning model generation support method for supporting generation of a learning model to be utilized in odor detection using an odor sensor that reacts to a plurality of types of odors, the method including:

(a) a step of acquiring sensor data output by the odor sensor under a specific measurement condition and condition data specifying the measurement condition, and inputting the acquired sensor data and condition data, as training data, to a machine learning engine for generating the learning model; and (b) a step of acquiring a predictive accuracy output by the machine learning engine in response to input of the training data, and based on the predictive accuracy, setting a new measurement condition for when the odor sensor newly outputs sensor data as the training data.

(Supplementary Note 8)

The learning model generation support method according to supplementary note 7, in which, in the (b) step, the new measurement condition is set, such that a predictive accuracy will be higher than the acquired predictive accuracy.

(Supplementary Note 9)

The learning model generation support method according to supplementary note 8, in which, in the (b) step, the new measurement condition is set, by executing sequential model-based optimization with the predictive accuracy and the measurement condition as parameters.

(Supplementary Note 10)

The learning model generation support method according to any of supplementary notes 7 to 9, in which the measurement condition includes at least temperature and humidity ambient to the odor sensor.

(Supplementary Note 11)

The learning model generation support method according to supplementary note 10, in which the measurement condition further includes information relating to an odor ambient to the odor sensor, other than an odor to be detected.

(Supplementary Note 12)

The learning model generation support method according to any of supplementary notes 7 to 11, further including:

(c) a step of presenting the set measurement condition.

(Supplementary Note 13)

A computer-readable recording medium that includes a program recorded thereon for supporting generation of a learning model to be utilized in odor detection using an odor sensor that reacts to a plurality of types of odors, with a computer, the program including instructions that cause the computer to carry out:
- (a) a step of acquiring sensor data output by the odor sensor under a specific measurement condition and condition data specifying the measurement condition, and inputting the acquired sensor data and the condition data, as training data, to a machine learning engine for generating the learning model; and
- (b) a step of acquiring a predictive accuracy output by the machine learning engine in response to input of the training data, and based on the predictive accuracy, setting a new measurement condition for when the odor sensor newly outputs sensor data as the training data.

(Supplementary Note 14)

The computer-readable recording medium according to supplementary note 13, in which, in the (b) step, the new measurement condition is set, such that a predictive accuracy will be higher than the acquired predictive accuracy.

(Supplementary Note 15)

The computer-readable recording medium according to supplementary note 14, in which, in the (b) step, the new measurement condition is set, by executing sequential model-based optimization with the predictive accuracy and the measurement condition as parameters.

(Supplementary Note 16)

The computer-readable recording medium according to any of supplementary notes 13 to 15, in which the measurement condition includes at least temperature and humidity ambient to the odor sensor.

(Supplementary Note 17)

The computer-readable recording medium according to supplementary note 16, in which the measurement condition further includes information relating to an odor ambient to the odor sensor, other than an odor to be detected.

(Supplementary Note 18)

The Computer-Readable Recording Medium According to any of Supplementary Notes 13 to 17, in which the Program Further Includes Instructions that Cause the Computer to Carry Out:
- (c) a step of presenting the set measurement condition.

Although the invention of the present application has been described above with reference to an example embodiment, the invention is not limited to the example embodiment described above. Various modifications apparent to those skilled in the art can be made to the configurations and details of the invention within the scope of the invention.

INDUSTRIAL APPLICABILITY

As described above, according to the invention, setting of measurement conditions can be supported, when generating a learning model for an odor sensor whose odor analysis target is not fixed. The invention is useful in various fields in which odor sensors are utilized.

LIST OF REFERENCE SIGNS

10 Learning model generation support apparatus
11 Data acquisition unit
12 Condition setting unit
13 Presentation unit
20 Detection apparatus
21 Odor sensor
22 Measurement condition detection sensor
24 Data communication unit
25 Display unit
26, 27 Window
28 Operation button
30 Learning model generation apparatus
31 Machine learning engine
32 Learning model
40 Communication terminal
41 Sensor unit
110 Computer
111 CPU
112 Main memory
113 Storage device
114 Input interface
115 Display controller
116 Data reader/writer
117 Communication interface
118 Input device
119 Display device
120 Recording medium
121 Bus

The invention claimed is:

1. A learning model generation support apparatus for supporting generation of a learning model to be utilized in odor detection using an odor sensor that reacts to a plurality of types of odors, the apparatus comprising a computer containing at least one processor, wherein the at least one processor is configured to function as:
a data acquisition unit configured to acquire sensor data output by the odor sensor under a specific measurement condition and condition data specifying the measurement condition, and input the acquired sensor data and the condition data, as training data, to a machine learning engine for generating the learning model;
a condition setting unit configured to acquire a predictive accuracy output by the machine learning engine in response to input of the training data, and based on the predictive accuracy, set a new measurement condition for when the odor sensor newly outputs sensor data as the training data;
wherein the condition setting unit sets the new measurement condition, by executing sequential model-based optimization with a predictive accuracy higher than the acquired predictive accuracy and the measurement condition as parameters, wherein repeating selection of a combination of candidate parameters and executing of simulations using the selected combination of the candidate parameters, changing the combination of the candidate parameters each time a simulation is executed, and specifying the combination of the candidate parameters whose predictive accuracy is higher than the acquired predictive accuracy as the new measurement condition.

2. The learning model generation support apparatus according to claim 1, wherein
the measurement condition includes at least temperature and humidity ambient to the odor sensor.

3. The learning model generation support apparatus according to claim 2, wherein
the measurement condition further includes information relating to an odor ambient to the odor sensor, other than an odor to be detected.

4. The learning model generation support apparatus according to claim 1, further comprising:
a presentation unit configured to present the set measurement condition.

5. The learning model generation support apparatus according to claim 1, wherein the new measurement conditions are set by setting a search space of parameters divided into a grid, with the number of parameters to be searched, allocating a combination of the parameters for every grid point, executing simulation for every combination, specifying the combination whose predictive accuracy is higher than the acquired predictive accuracy, and setting the specified combination as the new measurement conditions.

6. A learning model generation support method for supporting generation of a learning model to be utilized in odor detection using an odor sensor that reacts to a plurality of types of odors, the
method executed by a computer and comprising:
   acquiring sensor data output by the odor sensor under a specific measurement condition and the condition data specifying the measurement condition, and inputting the acquired sensor data and condition data, as training data, to a machine learning engine for generating the learning model;
   acquiring a predictive accuracy output by the machine learning engine in response to input of the training data, and based on the predictive accuracy, setting a new measurement condition for when the odor sensor newly outputs sensor data as the training data;
   wherein in the setting, the new measurement condition is set, by executing sequential model-based optimization with a predictive accuracy higher than the acquired predictive accuracy and the measurement condition as parameters, wherein repeating selection of a combination of candidate parameters and executing of simulations using the selected combination of the candidate parameters, changing the combination of the candidate parameters each time a simulation is executed, and specifying the combination of the candidate parameters whose predictive accuracy is higher than the acquired predictive accuracy as the new measurement condition.

7. The learning model generation support method according to claim 6, wherein
   the measurement condition includes at least temperature and humidity ambient to the odor sensor.

8. The learning model generation support method according to claim 7, wherein
   the measurement condition further includes information relating to an odor ambient to the odor sensor, other than an odor to be detected.

9. The learning model generation support method according to claim 6, further comprising:
   presenting the set measurement condition.

10. The learning model generation support method according to claim 6, wherein the new measurement conditions are set by setting a search space of parameters divided into a grid, with the number of parameters to be searched, allocating a combination of the parameters for every grid point, executing simulation for every combination, specifying the combination whose predictive accuracy is higher than the acquired predictive accuracy, and setting the specified combination as the new measurement conditions.

11. A non-transitory computer-readable recording medium that includes a program recorded thereon for supporting generation of a learning model to be utilized in odor detection using an odor sensor that reacts to a plurality of types of odors, with a computer, the program including instructions that cause the computer to carry out:
   acquiring sensor data output by the odor sensor under a specific measurement condition and the condition data specifying the measurement condition, and inputting the acquired sensor data and condition data, as training data, to a machine learning engine for generating the learning model;
   acquiring a predictive accuracy output by the machine learning engine in response to input of the training data, and based on the predictive accuracy, setting a new measurement condition for when the odor sensor newly outputs sensor data as the training data;
   wherein in the setting, the new measurement condition is set, by executing sequential model-based optimization with a predictive accuracy higher than the acquired predictive accuracy and the measurement condition as parameters, wherein repeating selection of a combination of candidate parameters and executing of simulations using the selected combination of the candidate parameters, changing the combination of the candidate parameters each time a simulation is executed, and specifying the combination of the candidate parameters whose predictive accuracy is higher than the acquired predictive accuracy as the new measurement condition.

12. The non-transitory computer-readable recording medium according to claim 11, wherein
   the measurement condition includes at least temperature and humidity ambient to the odor sensor.

13. The non-transitory computer-readable recording medium according to claim 12, wherein
   the measurement condition further includes information relating to an odor ambient to the odor sensor, other than an odor to be detected.

14. The non-transitory computer-readable recording medium according to claim 11, wherein
   the program further includes instructions that cause the computer to carry out:
   a step of presenting the set measurement condition.

15. The non-transitory computer-readable recording medium according to claim 11, wherein the new measurement conditions are set by setting a search space of parameters divided into a grid, with the number of parameters to be searched, allocating a combination of the parameters for every grid point, executing simulation for every combination, specifying the combination whose predictive accuracy is higher than the acquired predictive accuracy, and setting the specified combination as the new measurement conditions.

* * * * *